US008487081B2

(12) United States Patent
Vaulont et al.

(10) Patent No.: US 8,487,081 B2
(45) Date of Patent: Jul. 16, 2013

(54) ANTIBODIES SPECIFIC FOR HUMAN HEPCIDIN

(75) Inventors: Sophie Vaulont, Paris (FR); Hugues Gascan, Angers (FR); Josy Froger, Saint Clement de la Place (FR)

(73) Assignees: INSERM (Institut National de la Santé et de la Recherche Médicale), Paris (FR); Centre National de la Recherche Scientifique-CNRS, Paris (FR)

( * ) Notice: Subject to any disclaimer, the term of this patent is extended or adjusted under 35 U.S.C. 154(b) by 182 days.

(21) Appl. No.: 12/680,977

(22) PCT Filed: Oct. 2, 2008

(86) PCT No.: PCT/IB2008/003310
§ 371 (c)(1),
(2), (4) Date: May 19, 2010

(87) PCT Pub. No.: WO2009/044284
PCT Pub. Date: Apr. 9, 2009

(65) Prior Publication Data
US 2010/0285027 A1    Nov. 11, 2010

(30) Foreign Application Priority Data

Oct. 2, 2007  (EP) .................................. 07291196

(51) Int. Cl.
| | | |
|---|---|---|
| A61K 39/395 | (2006.01) | |
| A61P 7/06 | (2006.01) | |
| C07K 16/26 | (2006.01) | |
| C07H 21/04 | (2006.01) | |
| C12N 15/63 | (2006.01) | |
| C12P 21/00 | (2006.01) | |
| G01N 33/68 | (2006.01) | |

(52) U.S. Cl.
USPC .............. 530/387.1; 530/387.3; 530/389.2; 530/388.24; 435/7.1; 435/7.21; 435/70.2; 435/320.1; 435/336; 536/23.53

(58) Field of Classification Search
None
See application file for complete search history.

(56) References Cited

U.S. PATENT DOCUMENTS 6,632,927 B2 * 10/2003 Adair et al. ............... 530/387.3
8,017,737 B2 * 9/2011 Kulaksiz et al. ........... 530/387.9
2007/0224186 A1  9/2007 Kulaksiz et al.

FOREIGN PATENT DOCUMENTS

| EP | 1392345 | 3/2004 |
|---|---|---|
| WO | 02/098444 | 12/2002 |
| WO | 2004/058044 | 7/2004 |
| WO | 2008/089795 | 7/2008 |
| WO | 2008/097461 | 8/2008 |
| WO | 2009/044284 | 4/2009 |

OTHER PUBLICATIONS

Amit et al, Science vol. 233,747-753, 1986.*
Panka et al (Proc Natl Acad Sci USA vol. 85, 3080-3084.*
Rudikoff (Proc Natl Acad Sci USA 1982 vol. 79 p. 1979).*
Panka, 1988, Proc Natl Acad Sci USA, vol. 85, 3080-3084.*
Anderson et al., Curr. Opin. Gastroenterol., 25:129-135 (2009).
Bosze et al., J. Peptide Sci., 12(Suppl):592 (2006).
Dallalio et al., Br. J. Haematol., 122:996-1000 (2003).
Ganz et al., Blood, 112(10):4292-4297 (2008).
Ganz, Best Practice and Research Clinical Haematology, 18(2):171-182 (2005).
International Search Report in PCT/IB08/03310, mailed Feb. 24, 2009.
Jordan et al., J. Biol. Chem., 284:24155-24167 (2009).
Kawabata et al., Haematologica, 92(6):857-858 (2007).
Kemna et al., Blood, (2005).
Kemna et al., Haematologica, 93:90-97 (2008).
Kemna et al., Nat. Clin. Prac. Gast. Hep., 2:E1 (2005).
Krause et al., FEBS Lett., 480:147-150 (2000).
Kulaksiz et al., Gut, 53:735-743 (2004).
Kulaksiz et al., J. Endocrin., 184:361-370 (2005).
Nemeth et al., Blood, 101(7):2461-2463 (2003).
Nemeth et al., Blood, 107(1):328-333 (2006).
Nemeth et al., J. Clin. Invest., 113:1271-1276 (2004).
Notice of Opposition to a European Patent in EP 1 392 345, dated Dec. 30, 2009.
Notice of Opposition to a European Patent in EP 1 392 345, dated Dec. 23, 2009.
Park et al., J. Biol. Chem., 276(11):7806-7810 (2001).
Pigeon et al., J. Biol. Chem., 276:7811-7819 (2001).
Rivera et al., Blood, 106:2196-2199 (2005).
Roe et al., Br. J. Nutrition., 97:544-549 (2007).
Swinkels et al., Clin. Chem., 52(6):950-968 (2006).
Vallet et al., J. Biol. Chem., 272:21944-21949 (1997).
Valore et al., Blood Cells, Mol. and Dis., 40:132-138 (2008).
Viatte et al., Hematologie, 13(3):165-176 (2007).
Weiss et al., Eur. J. Clin. Invest., pp. 1-8 (2009).

* cited by examiner

*Primary Examiner* — Robert Landsman
*Assistant Examiner* — Ian Dang
(74) *Attorney, Agent, or Firm* — McAndrews, Held & Malloy, Ltd.

(57) ABSTRACT

The present invention relates to antigen-binding proteins having specificity for hepcidin, and their use for treating and diagnosing diseases associated with hepcidin.

13 Claims, 6 Drawing Sheets

SEQUENCE LISTING

```
<160> NUMBER OF SEQ ID NOS: 11

<210> SEQ ID NO 1
<211> LENGTH: 383
<212> TYPE: DNA
<213> ORGANISM: Mus musculus

<400> SEQUENCE: 1
gaggtacagc tggaggagtc tgggggaggt ttagtgcagc ctggagggtc cctgaaactc      60
tcctgtgcag cctctggatt cactttcagt agatatagca tgtcttgggt tcgccagact     120
ccagagaaga ggctggagtg ggtcgcatac attagtgatg gtggtggtag cacctactct     180
ccagacactg taaagggccg attcagcatt tccagagaca atgcccagaa caccctttac     240
ctacaaatga gcagtctgaa gtctgaggac acggccatat tttactgtgt aagacatgcg     300
cgattagagg gatacttcga tgtctggggc gcagggacct cggtcaccgt ctcctcagcc     360
aaaacgacac cccatctgtc tat                                            383

<210> SEQ ID NO 2
<211> LENGTH: 24
<212> TYPE: DNA
<213> ORGANISM: Mus musculus

<400> SEQUENCE: 2
ggattcactt tcagtagata tagc                                            24

<210> SEQ ID NO 3
<211> LENGTH: 24
<212> TYPE: DNA
<213> ORGANISM: Mus musculus

<400> SEQUENCE: 3
attagtgatg gtggtggtag cacc                                            24
```

```
<210> SEQ ID NO 4
<211> LENGTH: 36
<212> TYPE: DNA
<213> ORGANISM: Mus musculus

<400> SEQUENCE: 4
gtaagacatg cgcgattaga gggatacttc gatgtc                           36

<210> SEQ ID NO 5
<211> LENGTH: 651
<212> TYPE: DNA
<213> ORGANISM: Mus musculus

<400> SEQUENCE: 5
gacgtgttga cgcagtctcc agcttctgtg gctgtgtctc tagggcagag ggccaccata    60
tcctgcagag ccagtgaaag tgttgataat tatggcaata gttttatgaa ctggtaccag   120
cagaaaccag acagccacc caaactcctc atctatcgtg catccaacct agaatctggg    180
atccctgcca ggttcagtgg cagtgggtct aggacagact tcaccctcac cattaatcct   240
gtggaggctg atgatgttgc aacctattac tgtcagcaaa gtaatgagga tccgacgttc   300
ggtggaggca ccaagctgga aatcaaacgg gctgatgctg caccaactgt atccatcttc   360
ccaccatcca gtgagcagtt aacatctgga ggtgcctcag tcgtgtgctt cttgaacaac   420
ttctacccca agacatcaa tgtcaagtgg aagattgatg gcagtgaacg acaaaatggc    480
gtcctgaaca gttggactga tcaggacagc aaagacagca cctacagcat gagcagcacc   540
ctcacgttga cccaggacga gtatgaacga cataacagct atacctgtga ggccactcac   600
aagacatcaa cctcacccat tgtcaagagc ctcaacaggg gaaagtgtta g            651

<210> SEQ ID NO 6
<211> LENGTH: 30
<212> TYPE: DNA
<213> ORGANISM: Mus musculus

<400> SEQUENCE: 6
gaaagtgttg ataattatgg caatagtttt                                  30

<210> SEQ ID NO 7
<211> LENGTH: 9
<212> TYPE: DNA
<213> ORGANISM: Mus musculus

<400> SEQUENCE: 7 cgtgcatcc                                                          9

<210> SEQ ID NO 8
<211> LENGTH: 24
<212> TYPE: DNA
<213> ORGANISM: Mus musculus

<400> SEQUENCE: 8
cagcaaagta atgaggatcc gacg                                        24

<210> SEQ ID NO 9
<211> LENGTH: 26
<212> TYPE: PRT
<213> ORGANISM: Homo sapiens

<400> SEQUENCE: 9

Thr Asp Thr His Phe Pro Ile Cys Ile Phe Cys Cys Gly Cys Cys His
1               5                   10                  15
```

```
Arg Ser Lys Cys Gly Met Cys Cys Lys Thr
            20                  25

<210> SEQ ID NO 10
<211> LENGTH: 16
<212> TYPE: PRT
<213> ORGANISM: Homo sapiens

<400> SEQUENCE: 10

Pro Glu Leu Ala Pro Val Ser Ser Asn Leu Lys Tyr Thr Leu Asp Cys
1               5                   10                  15

<210> SEQ ID NO 11
<211> LENGTH: 12
<212> TYPE: PRT
<213> ORGANISM: Homo sapiens

<400> SEQUENCE: 11

Glu Asp Gln Val Asp Pro Arg Leu Ile Asp Gly Lys
1               5                   10
```

ANTIBODIES SPECIFIC FOR HUMAN HEPCIDIN

The present application is filed pursuant to 35 U.S.C. 371 as a U.S. National Phase application of International Patent Application No. PCT/IB08/03310, which was filed Oct. 2, 2008, claiming the benefit of priority to European Patent Application No. 07291196.9, which was filed on Oct. 2, 2007. The entire text of the aforementioned applications is incorporated herein by reference in its entirety.

The present invention relates to antibodies or fragments thereof recognizing the mature form of human hepcidin, and to their use for treating and diagnosing diseases associated with hepcidin.

Iron is an essential element required for growth and survival of almost every organism. Therefore, disturbances of iron metabolism have been implicated in a number of significant mammalian diseases, including, but not limited to iron deficiency anemia, hemosiderosis or the iron overload disease hemochromatosis (PIETRANGELO, Am J Physiol Gastrointest Liver Physiol, 282, G403-14, 2002; ANDREWS, Annu Rev Genomics Hum Genet, 1, 75-98, 2000; PHILPOTT, Hepatology, 35, 993-1001, 2002; ANDERSON & POWELL, Int J Hematol, 76, 203-7, 2002; BEUTLER et al., Drug Metab Dispos, 29, 495-9, 2001).

Iron deficiency is the most common nutritional disorder in the world. As many as 4-5 billion people (i.e., 65-80% of the world's population) may be iron deficient, and 2 billion people (over 30% of the world's population, mostly children and women of childbearing age) are anemic, mainly due to iron deficiency. Iron deficiency affects more people than any other condition, constituting a public health condition of epidemic proportions.

In mammals, the iron balance is primarily regulated at the level of duodenal absorption of dietary iron. Following absorption, ferric iron is loaded into apo-transferrin in the circulation and transported to the tissues, including erythroid precursors, where it is taken up by transferrin receptor-mediated endocytosis. Reticuloendothelial macrophages play a major role in the recycling of iron from the degradation of hemoglobin of senescent erythrocytes, while hepatocytes contain most of the iron stores of the organism in ferritin polymers. A feedback mechanism exists that enhances iron absorption in individuals who are iron deficient, whereas iron absorption is reduced in persons with iron overload. In hereditary hemochromatosis (HH), however, this regulatory mechanism seems to be impaired; despite iron overload, elevated amounts of iron are absorbed from the diet and lead to accumulation of excess iron in internal organs, resulting in organ dysfunction and failure. The molecular mechanism by which the intestine responds to alterations in body iron requirements is poorly understood. In this context, hepcidin, a recently identified mammalian peptide (KRAUSE et al., FEBS Lett, 480, 147-50, 2000; PARK et al., J Biol Chem, 276, 7806-10, 2001) was shown to be a key signaling component regulating iron homeostasis (NICOLAS et al., Proc Natl Acad Sci USA, 99, 4596-601, 2002).

Hepcidin regulates iron homeostasis by binding to the cellular iron exporter ferroportin and causing its internalization and degradation (NEMETH et al., Science, 306, 2090-3, 2004). The consequence of the degradation of ferroportin is the retention of iron in the cells and thus a diminution of circulating iron. By this mechanism, hepcidin decreases iron efflux from iron exporting tissues into plasma and thus reduces dietary iron absorption, release of recycled iron from macrophages, release of iron stored in hepatocytes, ant transfer of iron across placenta.

Hepcidin is a small cysteine-rich peptide predominantly produced in the liver. This molecule regulates the absorption of iron in the intestine and inhibits release of iron from macrophages. Hepcidin was initially isolated from human plasma and urine as a 25 amino acid (aa) peptide exhibiting antimicrobial activity (KRAUSE et al., FEBS Lett, 480, 147-50, 2000; PARK et al., J Biol Chem, 276, 7806-10, 2001). Hepcidin cDNAs encoding an 83 aa precursor in mice and an 84 aa precursor in rat and man, including a putative 24 aa signal peptide, were subsequently identified searching for liver-specific genes that were regulated by iron (PIGEON et al., J Biol Chem, 276, 7811-9, 2001). Human hepcidin is expressed as an 84 amino acid prepropeptide that is amino terminally processed to a 60 amino acid residue precursor (prohepcidin) of about 10 kDa, which is further processed into a 25 amino acid mature peptide (hepcidin-25) of about 3 kDa. In addition to the 25-amino acid form, 20- and 22-amino acid forms truncated at the N-terminus were also detected in urine (PARK et al., J Biol Chem, 276, 7806-10, 2001). However, these N-truncated variants appear to have no iron-regulatory function (RIVERA et al., Blood, 106, 2196-9, 2005; NEMETH et al., Blood, 107, 328-33, 2006). Accordingly, it is generally admitted that hepcidin-25 is the bioactive form which is mainly responsible of the hypoferremic effect of hepcidin.

Hepcidin is a central regulator of iron homeostasis. Hepcidin deficiency plays a central role in most iron overload disorders, and it has also be shown that hepcidin excess is involved in several forms of anemia. For example, Nicolas G. et al (2002) showed that overexpression of hepcidin resulted in severe anemia in transgenic mice (NICOLAS et al., Proc Natl Acad Sci USA, 99, 4596-601, 2002). A recent study reported that hepcidin is a key mediator of anemia of inflammation (NEMETH et al., Blood, 101, 2461-3, 2003). Moreover, abnormal high concentration of hepcidin was reported in anemia with different aetiologies, such as anemia associated with renal disease (TOMOSUGI et al., Blood, 108, 1381-7, 2006), anemia associated with severe sepsis (KEMNA et al., Blood, 106, 3268-70, 2005), anemia associated with Crohn's disease (SEMRIN et al., Inflamm Bowel Dis, 12, 1101-6, 2006) and iron refractory anemia associated with hepatic adenomas (WEINSTEIN et al., Blood, 100, 3776-81, 2002).

Due to involvement of hepcidin in disorders of iron homeostasis, various assays for its detection and quantification in plasma or urine in view of the diagnosis and monitoring of these disorders have been proposed.

However, the development of immunochemical reagents has been hampered by the lack of availability of anti-hepcidin antibodies. An immunochemical assay using polyclonal anti-hepcidin rabbit antibodies has been described (NEMETH et al., Blood, 101, 2461-3, 2003), but it only allows to quantify hepcidin in urin, and not in plasma. Rabbit antisera produced against aa 28-47 (EG(1)-HepN and EG(2)-HepN) and aa 70-84 (EG(1)-HepC) of prohepcidin have also been described (PCT application WO 2004/058044; (KULAKSIZ et al., Gut, 53, 735-43, 2004). These antisera detected prohepcidin in human serum; however, none of them recognized the bioactive hepcidin-25.

Until now, no antibody able to recognize hepcidin-25 in serum has been described, and the only available assays for determination of hepcidin-25 in serum are based on mass spectrometry (TOMOSUGI et al., Blood, 108, 1381-7, 2006) (MURPHY et al., Blood, 110, 1048-54, 2007).

Furthermore, antibodies acting as hepcidin antagonists, i.e. able to inhibit the binding of hepcidin to ferroportin and the subsequent internalization and degradation of ferroportin would be useful in the treatment of conditions resulting from an excess of hepcidin.

Thus, antibodies recognizing hepcidin-25 and allowing its determination in serum, and further able to inhibit the binding of hepcidin to ferroportin appear highly desirable.

The inventors have now succeeded in obtaining such an antibody.

This monoclonal antibody, hereinafter designated "AN-LP1" is produced by the hybridoma deposited in accordance with the terms of Budapest Treaty, at the CNCM (Collection Nationale de Cultures de Microorganismes, Institut Pasteur, 25 rue du Docteur Roux, 75724 Paris Cedex 15, France), on Aug. 14, 2007, under the deposit number I-3794.

The inventors have cloned and sequenced the variable domain (VL) of the light chain, and the variable domain (VH) of the heavy chain of the monoclonal antibody AN-LP1. The limits of the sequences encoding the complementarity determining regions (CDRs) of said antibody have been obtained, classically, by aligning these VH and VL sequences against the IMGT reference database (LEFRANC et al., Nucl. Acids Res., 33, Database issue D593-597, 2005), using the software program IMGT/V-QUEST (GIUDICELLI et al. Nucl. Acids Res., 32, Web Server issueW435-440, 2004). These sequences are described below in Table 1 (for the heavy chain) and Table 2 (for the light chain).

TABLE 1

| mAb AN-LP1 Domains | Sequence |
|---|---|
| VH | GAGGTACAGCTGGAGGAGTCTGGGGGAGGTTTAGTGCAGC CTGGAGGGTCCCTGAAACTCTCCTGTGCAGCCTCTGGATT CACTTTCAGTAGATATAGCATGTCTTGGGTTCGCCAGACT CCAGAGAAGAGGCTGGAGTGGGTCGCATACATTAGTGATG GTGGTGGTAGCACCTACTCTCCAGACACTGTAAAGGGCCG ATTCAGCATTTCCAGAGACAATGCCCAGAACACCCTTTAC CTACAAATGAGCAGTCTGAAGTCTGAGGACACGGCCATAT TTTACTGTGTAAGACATGCGCGATTAGAGGGATACTTCGA TGTCTGGGGCGCAGGGACCTCGGTCACCGTCTCCTCAGCC AAAACGACACCCCATCTGTCTAT (SEQ ID NO: 1) |
| VH-CDR1 | GGATTCACTTTCAGTAGATATAGC (SEQ ID NO: 2) |
| VH-CDR2 | ATTAGTGATGGTGGTGGTAGCACC (SEQ ID NO: 3) |
| VH-CDR3 | GTAAGACATGCGCGATTAGAGGGATACTTCGATGTC (SEQ ID NO: 4) |

TABLE 2

| mAb AN-LP1 Domains | Sequence |
|---|---|
| VL | GACGTGTTGACGCAGTCTCCAGCTTCTGTGGCTGTGTCT CTAGGGCAGAGGGCCACCATATCCTGCAGAGCCAGTGAA AGTGTTGATAATTATGGCAATAGTTTTATGAACTGGTAC CAGCAGAAACCAGGACAGCCACCCAAACTCCTCATCTAT CGTGCATCCAACCTAGAATCTGGGATCCCTGCCAGGTTC AGTGGCAGTGGGTCTAGGACAGACTTCACCCTCACCATT AATCCTGTGGAGGCTGATGATGTTGCAACCTATTACTGT CAGCAAAGTAATGAGGATCCGACGTTCGGTGGAGGCACC AAGCTGGAAATCAAACGGGCTGATGCTGCACCAACTGTA TCCATCTTCCCACCATCCAGTGAGCAGTTAACATCTGGA GGTGCCTCAGTCGTGTGCTTCTTGAACAACTTCTACCCC AAAGACATCAATGTCAAGTGGAAGATTGATGGCAGTGAA CGACAAAATGGCGTCCTGAACAGTTGGACTGATCAGGAC AGCAAAGACAGCACCTACAGCATGAGCAGCACCCTCACG TTGACCCAGGACGAGTATGAACGACATAACAGCTATACC |

TABLE 2-continued

| mAb AN-LP1 Domains | Sequence |
|---|---|
| | TGTGAGGCCACTCACAAGACATCAACCTCACCCATTGTC AAGAGCCTCAACAGGGGAAAGTGTTAG (SEQ ID NO: 5) |
| VL-CDR1 | GAAAGTGTTGATAATTATGGCAATAGTTTT (SEQ ID NO: 6) |
| VL-CDR2 | CGTGCATCC (SEQ ID NO: 7) |
| VL-CDR3 | CAGCAAAGTAATGAGGATCCGACG (SEQ ID NO: 8) |

An object of the present invention is an antigen-binding protein characterized in that it is capable of binding human hepcidin-25, and in that it comprises at least the VH-CDR3 of the heavy chain and the VL-CDR3 of the light chain of the antibody AN-LP1.

According to a preferred embodiment, said antigen-binding protein further comprises the VH-CDR1 of the heavy chain and the VL-CDR1 of the light chain of the antibody AN-LP1.

According to another preferred embodiment, said antigen-binding protein further comprises the VH-CDR2 of the heavy chain and the VL-CDR2 of the light chain of the antibody AN-LP1.

The VH-CDR3 and the VL-CDR3 of AN-LP1 are respectively encoded by SEQ ID NO: 4 and SEQ ID NO: 8. The VH-CDR1 and the VL-CDR1 of AN-LP1 are respectively encoded by SEQ ID NO: 2 and SEQ ID NO: 6. The VH-CDR2 and the VL-CDR2 of AN-LP1 are respectively encoded by SEQ ID NO: 3 and SEQ ID NO: 7.

Antigen binding proteins of the invention encompass in particular:

a) the monoclonal antibody AN-LP1 produced by the hybridoma CNCM I-3794;
b) the antigen binding fragments of the antibody AN-LP1;
c) the chimeric or humanized antibodies obtained from AN-LP1;
d) the antigen-binding fragments of the antibodies c) above.

Unless otherwise specified, the term "hepcidin-25" herein refers to the human hepcidin polypeptide having the following sequence:

DTHFPICIFCCGCCHRSKCGMCCKT.    (SEQ ID NO: 9)

The CDRs (complementarity determining regions) of an antibody are the portions of the variable domains which are involved in antigen recognition specificity. Each light and heavy chain of an immunoglobulin has three CDRs, designated VL-CDR1, VL-CDR2, VL-CDR3 and VH-CDR1, VH-CDR2, VH-CDR3, respectively.

Antigen-binding fragments of an antibody contain the variable domains comprising the CDRs of said antibody. The basic antigen-binding fragments include Fv, dsFv, scFv, Fab, Fab', F(ab')2.

Fv fragments consist of the VL and VH domains of an antibody associated together by hydrophobic interactions; in dsFv fragments, the VH::VL heterodimer is stabilised by a disulphide bond; in scFv fragments, the VL and VH domains are connected to one another via a flexible peptide linker thus forming a single-chain protein. Fab fragments are obtainable by papain digestion of an antibody; they comprise the entire L chain, and a about a half of the N-terminal side of H chain, bound together through a disulfide bond. The F(ab')2 fragment can be produced by pepsin digestion of an antibody; it comprises two Fab fragments, and additionally a portion of the hinge region of the immunoglobulin molecule. The Fab' fragments are obtainable from F(ab')2 fragments by cutting a disulfide bond in the hinge region. F(ab')2 fragments are divalent, i.e. they comprise two antigen-binding sites, like the native immunoglobulin molecule; on the other hand, Fv, dsFv, scFv, Fab, and Fab' fragments are monovalent, i.e. they comprise a single antigen-binding site.

These basic antigen-binding fragments can be combined together to obtain multivalent antigen-binding fragments, such as diabodies, tribodies or tetrabodies. These multivalent antigen-binding fragments are also part of the present invention.

The terms "chimeric antibody" herein refers to an engineered antibody having the variable domains of the monoclonal antibody from which it is derived, and having constant domains from another antibody, preferably a from a human antibody.

The term "humanized antibody" herein refers to an antibody which has been engineered in order to reduce its immunogenicity, while retaining its antigen-binding specificity by replacing as much as possible of the murine sequences by their human counterparts. Within the variable domains, these sequence replacements generally target the framework regions (FRs), i.e the amino acid sequences interposed between the CDRs. However, some methods of humanizing antibodies involve sequence replacements within the CDRs 1 and 2.

The chimeric and humanized antibodies of the invention can belong to any class of immunoglobulins. Preferably, they will belong to a subclass of the IgG class such as IgG1, IgG2, IgG3 or IgG4.

According to a preferred embodiment of an antigen-binding protein of the invention, it is able to inhibit the binding of hepcidin to ferroportin, thereby inhibiting the degradation of ferroportin.

The ability to inhibit the binding of hepcidin to ferroportin can easily be tested using for instance, an in vitro assay using cells expressing ferroportin at their surface. In presence of hepcidin, ferroportin is internalized and degraded. In presence of an inhibitor of the binding of hepcidin to ferroportin, ferroportin internalization and degradation are reduced or suppressed. The evaluation of the ferroportin level allows to determine the inhibitory properties.

Antigen-binding proteins in accordance with the invention can be obtained by conventional techniques. For instance, antigen-binding fragments like Fv, Fab or F(ab')2, may be obtained by enzyme digestion of the whole antibody.

These fragments as well as other monovalent and multivalent antigen-binding fragments, and chimeric or humanized antibodies, can also be prepared by classical genetic engineering techniques, such as those described by SAMBROOK et al. [MOLECULAR CLONING, A LABORATORY MANUAL, 2nd Ed., Cold Spring Harbor Laboratory Press, Cold Spring Harbor, N.Y., (1989)].

Polynucleotides encoding the variable regions of the antibody AN-LP1 or the CDRs thereof, can, for example, be obtained by cloning said regions from a cDNA library of the hybridoma CNCM I-3794. They can also be prepared, completely or partially, by nucleic acid synthesis, based on the nucleotide sequences provided herein.

Methods for preparing recombinant antigen-binding fragments, or chimeric antibodies by combining the variable regions of an antibody with appropriate linkers, or with the constant regions of another antibody, are well known in themselves.

Methods for humanizing antibodies are also well known in the art and are described for instance by ROUTLEDGE et al. ["Reshaping antibodies for therapy", in Protein Engineering of Antibody Molecules for Prophylactic and Therapeutic Applications in Man, 13-44, Academic Titles, Nottingham, England (1993)] or by ROGUSKA et al. Protein Engineering, 9(10), 895-904, (1996)]. These methods can also apply to antigen-binding fragments, such as scFvs.

By way of example, the method known as "resurfacing" consists in replacing the set of surface residues in the frameworks of the variable region of a nonhuman antibody with a human set of surface residues, while the method known as CDR grafting consists of transferring the CDRs from a nonhuman antibody into the framework regions of a human antibody. CDR grafting is generally completed by framework optimization, consisting in the replacement of some residues of the human framework, in order to optimize the binding affinity.

The step of framework optimization has been recently simplified by the use of combinatorial libraries (ROSOK. et al. J. Biol. Chem. 271, 22611-22618, 1996; BACA et al. J. Biol. Chem. 272, 10678-10684, 1997).

Another recent strategy for antibody humanization preserves only the original nonhuman CDR3 sequences of light and heavy chain while the remaining sequence is selected from naïve human V gene libraries (RADER et al., *Proc. Natl. Acad. Sci. U.S.A.* 95, 8910-8915, 1998).

A subject of the present invention is also any polynucleotide encoding an antigen-binding protein of the invention comprising the CDRs of the antibody AN-LP1, and also any recombinant vector, in particular any expression vector, comprising said polynucleotide.

A subject of the present invention is also any cell expressing an antigen-binding protein in accordance with the invention comprising the CDRs of the antibody AN-LP1. This encompasses in particular the hybridoma CNCM I-3794, and also any host cell genetically transformed with a polynucleotide of the invention.

Polynucleotides of the invention may advantageously comprise, besides a sequence encoding an antigen-binding protein in accordance with the invention, a sequence encoding a signal peptide allowing secretion of said protein. They may also comprise one or more sequence(s) encoding one or more marker peptide(s) for detecting, and/or facilitating the purification of, said protein.

Expression vectors in accordance with the invention comprise at least one nucleic acid sequence encoding an antigen-binding protein in accordance with the invention, associated with transcription- and translation-controlling elements which are active in the host cell chosen. There is a broad variety of host vectors, known in themselves, which can be used to construct expression vectors in accordance with the invention; the choice of an appropriate vector depends mainly on the host cell intended to be used.

Host cells which can be used in the context of the present invention can be prokaryotic or eukaryotic cells. Examples of eukaryotic host cells include bacteria such as *E. coli*. Among the eukaryotic cells which can be used, mention will in particular be made of plant cells (in the case of plantibodies), cells from yeast, such as *Saccharomyces, Kluyveromyces*, or *Pichia pastoris*, insect cells, such as *Drosophila* or *Spodoptera* cells, and mammalian cells such as HeLa, CHO, 3T3, C127, BHK, Heck 293, COS, etc., cells.

The construction of expression vectors in accordance with the invention and the transformation of the host cells can be carried out by the conventional techniques of molecular biology.

A subject of the invention is also a method for producing an antigen-binding protein in accordance with the invention, characterized in that it comprises culturing at least one cell in accordance with the invention, and recovering said protein from said culture.

If the protein is secreted, it can be recovered directly from the culture medium; if not, cell lysis will be carried out beforehand.

The protein can then be purified from the culture medium or from the cell lysate, by conventional procedures, known in themselves to those skilled in the art, for example by fractionated precipitation, in particular precipitation with ammonium sulfate, electrophoresis, gel filtration, affinity chromatography, etc.

If desired, the antigen-binding proteins of the invention can be further modified in order for instance, to facilitate their detection, to facilitate their administration in vivo, or to enhance their therapeutic properties. By way of non-limitative examples, they may be labelled with a detectable molecule or substance, such as a fluorescent molecule, a radioactive molecule, a spin label for nuclear magnetic resonance (NMR) imaging, or any others labels known in the art, they may also be coupled with molecules, such as polyethylene glycol, which prolong their plasma half-life.

An antibody of the invention may be labelled with a radioactive molecule by any method known to the art. For example radioactive molecules include but are not limited radioactive atom for scintigraphic studies such as I123, I124, In111, Re186, Re188. Antibodies of the invention may be also labelled with (also known as magnetic resonance imaging, mri), such as iodine-123, iodine-131, indium-Ill, fluorine-19, carbon-13, nitrogen-15, oxygen-17, gadolinium, manganese or iron.

The antigen-binding proteins of the invention can be used for diagnostic of hepcidin-related diseases.

In particular, they can be used for detecting hepcidin, and/or evaluating its amount in a biological sample, in particular blood, urine, amniotic fluid samples, or organ biopsies. Therefore they can be used for diagnosing all diseases associated with abnormal hepcidin levels, whether they are associated with hepcidin excess or with hepcidin deficiency.

An object of the invention is a method for detecting hepcidin, and/or evaluating its amount in a biological sample, in particular a serum or plasma sample, from an human subject, wherein said method comprises contacting said sample with an antigen-binding protein of the invention under conditions allowing the formation of an immune complex between hepcidin and said antigen-binding protein, and detecting or measuring the immune complex formed.

The immune complex formed can be detected or measured by a variety of methods using standard techniques, including, by way of non-limitative examples, enzyme-linked immunosorbent assay (ELISA) or other solid phase immunoassays, radioimmunoassay, electrophoresis, immunofluorescence, or Western blot.

A further object of the invention is a method for diagnosing a disease associated with abnormal hepcidin levels, wherein said method comprising evaluating the amount of hepcidin, as indicated above, in a biological sample from a subject to be tested, and comparing the determined amount with a control value of hepcidin in a normal subject.

The method of the invention can be used for diagnosing diseases associated with excessive hepcidin levels, such as anemia of chronic disease, anemia of cancer, and anemia of renal insufficiency as well as for diagnosing diseases associated with insufficient hepcidin levels, such as congenital chronic anemias or iron deficient anemia (chronic bleeding, ulcerative gastritis . . . ) or with a relative or complete hepcidin deficiency such as hereditary hemochromatosis.

The invention also provides kits comprising an antigen-binding protein of the invention, associated with one or more devices and/or reagents for performing an immunoassay. For instance, kits of the invention can contain an antigen-binding protein of the invention coupled to a solid support, e.g., a tissue culture plate or beads (e.g., sepharose beads), and reagents for performing an immunoassay.

The antigen-binding proteins of the invention, able to inhibit the binding of hepcidin to ferroportin can also be used as medicaments. They are useful for the treatment of diseases associated with an excess of hepcidin, in particular anemia of cancer, anemia of renal insufficiency and anemia of chronic disease. Anemia of chronic disease, also known as anemia of inflammation, is likewise the most frequent anemia in hospitalized patients. This mild to moderate normocytic to microcytic anemia is found with a frequency between 8% and 95% in patients suffering from diseases that are associated with chronic immune activation, such as autoimmune disorders including rheumatoid arthritis and malignancies and chronic infections including HIV.

The invention thus provides a method of treating anemia in a patient in need thereof, comprising administering to said patient a therapeutically effective amount of an antigen-binding protein of the invention, able to inhibit the binding of hepcidin to ferroportin.

The conditions treatable by the antigen-binding proteins of the present invention include for instance anemia of chronic disease, anemia associated with a decline or loss of kidney function (chronic renal failure), anemia associated with myelosuppressive therapy, such as chemotherapeutic or antiviral drugs (such as AZT), anemia associated with the progression of non-myeloid cancers, anemia associated with viral infections (such as HIV), anemia in patients with Crohn's disease, anemia with chronic immune activation, late-life anemia and anemia of thermal injury.

The invention also provides pharmaceutical compositions comprising an antigen-binding protein of the invention. The antigen-binding proteins of the invention can be administered by themselves, or mixed with pharmaceutically acceptable carriers or excipient(s). They can be used systemically or locally. A preferred route of administration is the parenteral route, including for instance intramuscular, subcutaneous, intravenous, or intraperitoneal injections. The oral route can also be used, provided that the medicament is in a form suitable for oral administration, able to protect the active principle from the gastric and) intestinal enzymes.

The present invention will be further illustrated by the additional description which follows, which refers to examples describing the monoclonal antibody AN-LP1. It should be understood however that these examples are given only by way of illustration of the invention and do not constitute in any way a limitation thereof.

EXAMPLE 1

Production and Characterization of the Anti-Hepcidin Antibody AN-LP1

The hepcidin binding properties of AN-LP1 produced by hybridoma CNCM I-3794 were tested by ELISA. Synthetic human hepcidin-25 was coated on 96-well boxes, with a concentration of 1-10 microgram/ml in 100 mM carbonate buffer, pH 9.5. One part of the wells is coated with an irrelevant peptide (PELAPVSSNLKYTLDC, SEQ ID NO: 10) to be able to determine the specific component of measured signal. After one night of contact, the wells are washed 3 times with a solution of PBS/0.05% tween 20, then saturated with a solution of 0.1M Tris 20%, sucrose pH 7.8. The mouse serums are added in duplicates, with 10-fold serial dilutions. After a 6 h incubation, the wells were washed three times with a solution of PBS 0.05%, tween 20 and an anti-mouse antibody coupled with peroxidase (Biosource) diluted to 1/5,000 in PBS, 0.1% BSA, 0.01% Tween 20 was added for an additional 1 h30-2 h. Binding of the antibody was revealed using ABTS [2,2'-azino-bis(3-ethylbenzthiazoline-6-sulfonic acid)] as a substrate, and the reading was carried out at 405 nm.

Figure 1:
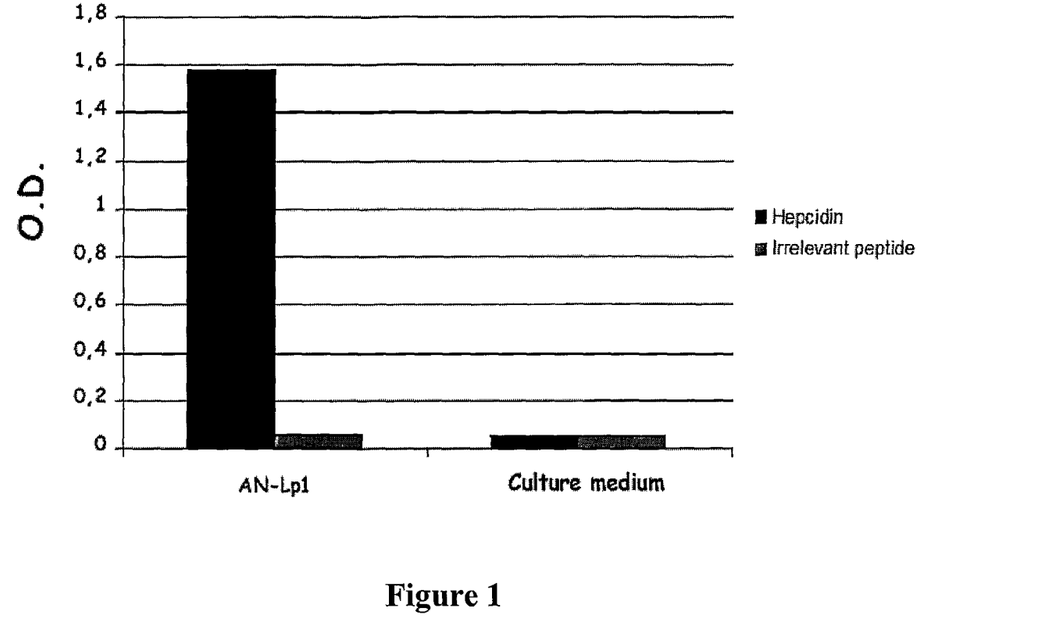
FIG. 1 depicts the binding of AN-LP1 to human hepcidin-25, relative to a control peptide.

The results are illustrated by FIG. 1. They show that AN-LP1 specifically binds human hepcidin-25 coated on the wells, and does not bind the control peptide.

Cells of the hybridoma CNCM I-3794, producing the antibody, were used for ascites production of the AN-LP1 antibody. The mice were treated with an I.P. injection of 0.5 ml pristane, 8 days before the injection of $10^7$ hybridoma cells. Two weeks later, the ascites were withdrawn, and the antibody purified by the technique of sequential precipitation with caprylic acid. The caprylic acid precipitates the proteins of a molecular weight lower than 100-120 kDa. The precipitate was spin down, and immunoglobulins present in the supernatant were then precipitated using ammonium sulphate at a 45% final concentration (w/v). These two successive precipitations make it possible to obtain, starting from 2 mice, 30 milligrams of purified antibody.

Figure 2:
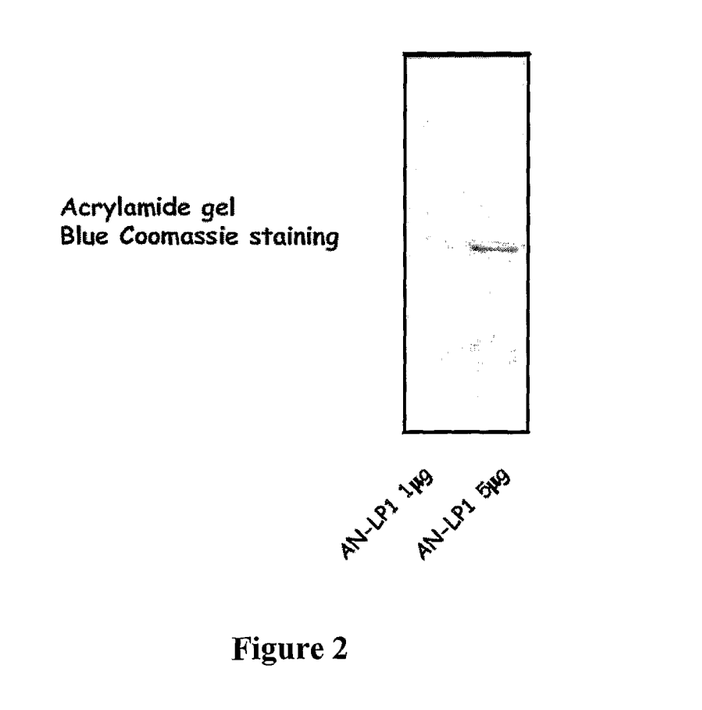
FIG. 2 depicts an SDS-PAGE of purified AN-LP1.

The secreted AN-LP1 immunoglobulin is an IgG1 Kappa. The results of analysis by SDS-PAGE are presented on FIG. 2. These results show that AN-LP1 presents the conventional features of IgG (heavy chain 50 kDa, light chain 25 kDa).

Further experiments were performed in order to better characterize the antibody.

1—Dot Blot Analyses:

Samples of synthetic human hepcidin (100 to 500 ng) or synthetic mouse) hepcidin (500 ng) (Peptide International, Louisville, Ky., USA), or of 10 or 400 of sera from a patient with an inflammatory disease, or from a healthy volunteer, were used. In one experiment, one sample of synthetic human hepcidin (500 ng) was treated with Laemmli buffer. The samples were directly spotted onto the nitrocellulose membrane and allowed to dry overnight. Non-specific sites were blocked by soaking the membrane in 5% skim milk in TBS-T (1 hr, at room temperature).

The primary antibodies (AN-LP1 antibody, or irrelevant antibody HPC4 directed against the epitope EDQVDPRLIDGK (SEQ ID NO: 11) of human protein C) were added at a dilution of 1:200 from a solution at 6 mg/ml. Incubation was performed for 2 h at room temperature or overnight at +4° C.

After 3 washes with TBS-T, the membranes were incubated with the secondary antibody conjugated with horseradish peroxidase (1:5000) for 1 h at room temperature.

The signals were visualized by chemiluminescence using an ECL reagent, followed by autoradiography.

Figure 3:
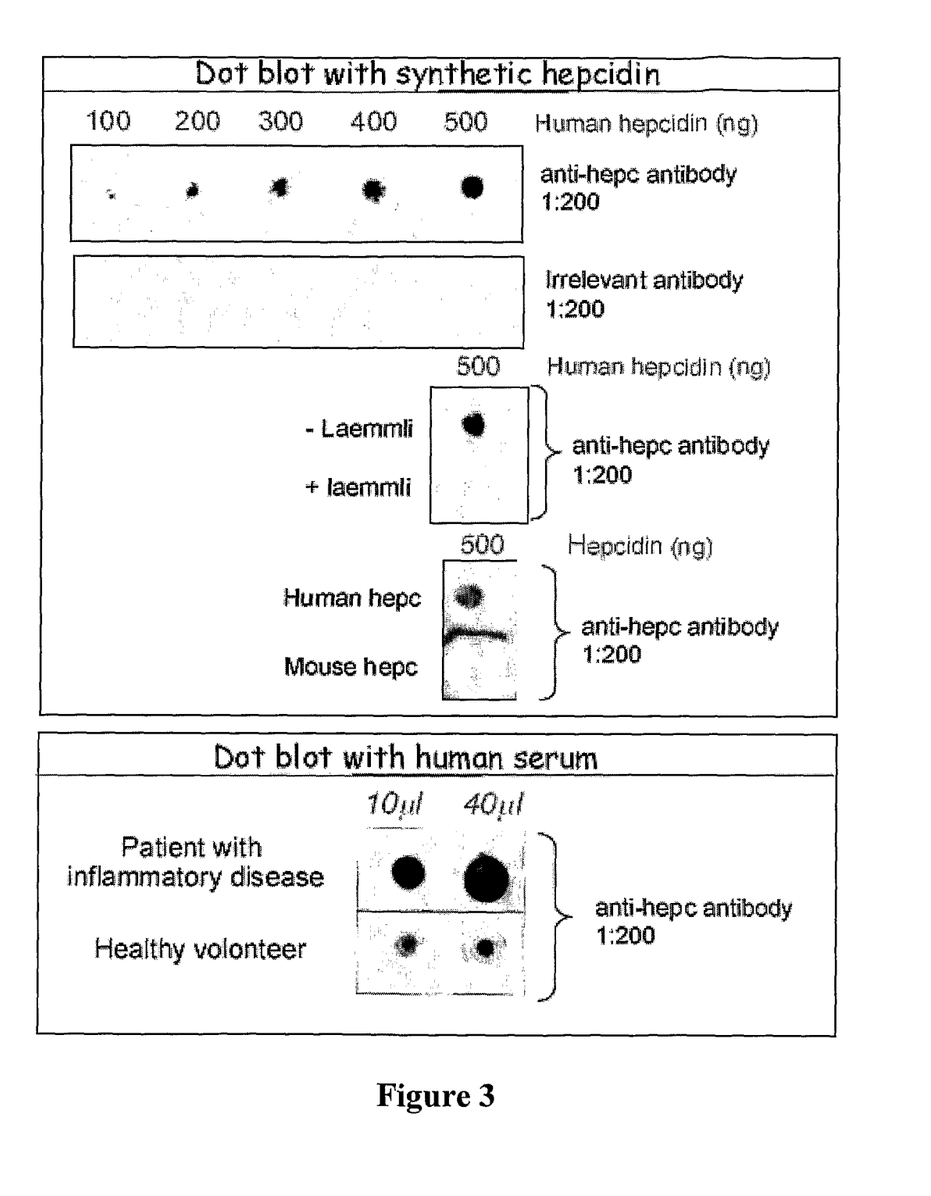
FIG. 3 depicts a dot blot analysis of AN-LP1 binding to hepcidin.

The results are presented in FIG. 3. These results show:
that revelation of hepcidin with the antibody AN-LP1 is specific (no signal with the irrelevant antibody HPC4)
that revelation of hepcidin with the antibody AN-LP1 requires the native structure of the peptide (no signal when the sample is treated with Laemmli)
that the antibody AN-LP1 do not cross-react with murine hepcidin-25;
that serum hepcidin from human samples is well recognized by the antibody AN-LP1.

2—Western Blot Analysis:

Samples of synthetic human or mouse hepcidin (Peptide International) were separated in a 16% Novex® Tricine gel in non-reducing conditions and blotting was performed onto PVDF membrane for 1 h at room temperature. Non-specific sites were blocked by soaking the membrane in 5% skim milk in TBS-T (2 hr, room temperature).

Incubation with the primary antibody (AN-LP1 antibody, 6 mg/ml, diluted at 1:100) was performed overnight at +4° C.

After 3 washes with TBS-T, the membrane was incubated with the secondary antibody conjugated with horseradish peroxidase (1:5000) for 1 h at room temperature.

The signal was visualized by chemiluminescence using an ECL reagent, followed by autoradiography.

Figure 4:
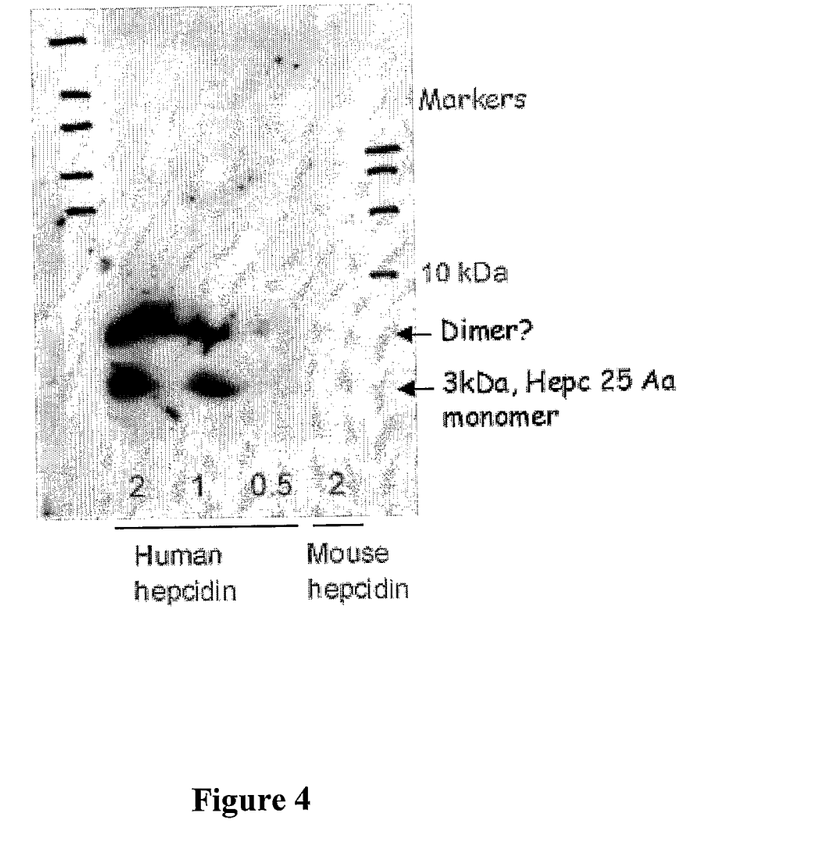
FIG. 4 depicts a Western blot of the binding of AN-LP1 to human and mouse hepcidin.

The results are presented in FIG. 4. These results show that the AN-LP1 antibody is efficient for detecting human hepcidin in Western Blot analysis revealing a product of the correct size (approximately 3 kDa for the peptide of 25 AA) and an additional band most likely corresponding to dimers of hepcidin. In contrast, no signal is observed for mouse hepcidin, confirming the results of dot-blot analyses.

3—Immunohistochemistry:

Immunochemistry was performed on paraffine-embedded human liver. The AN-LP1 antibody was used at dilution of 1:50 overnight at +4° C. After incubation with the secondary antibody conjugated with horseradish peroxidase, sections were revealed with diaminobenzidine.

Figure 5:
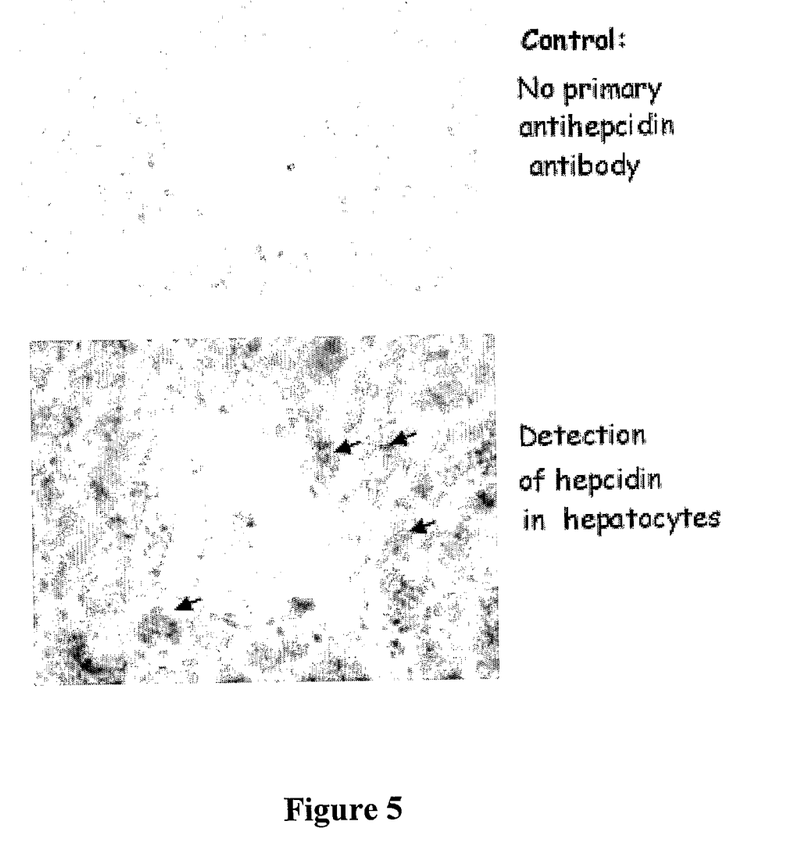
FIG. 5 depicts immunohistochemical staining of hepatocytes with AN-LP1.

The results are presented in FIG. 5. These results show that the AN-LP1 antibody is efficient for revealing hepcidin in human liver biopsies

EXAMPLE 2

Functional Properties of the Antibody AN-LP1

A screening test for hepcidin biological activity was developed. This test is based on the capacity of the hepcidin to degrade the iron exporter, ferroportin. It consists in incubating macrophages (J774murine cell line), which express ferroportin, in the presence of hepcidin during a few hours. If the hepcidin is biologically active, it will bind to ferroportin and induce its degradation.

More specifically:

J774 cells were treated overnight with 200 μM iron-NTA to induce ferroportin production. Synthetic hepcidin-25 (100 nM) alone, or linked to KLH (200 nM), or an irrelevant peptide linked to KLH (100 nM) were added to the cell culture. A culture with no peptide added was used as a control.

After incubation for 5 h at 37° C., the cells were washed, then lysed. Membrane extracts were prepared, and analyzed by Western blot with anti-ferroportin antibodies. The results are presented in FIG. 6 A (Lane 1: control)

Figure 6:
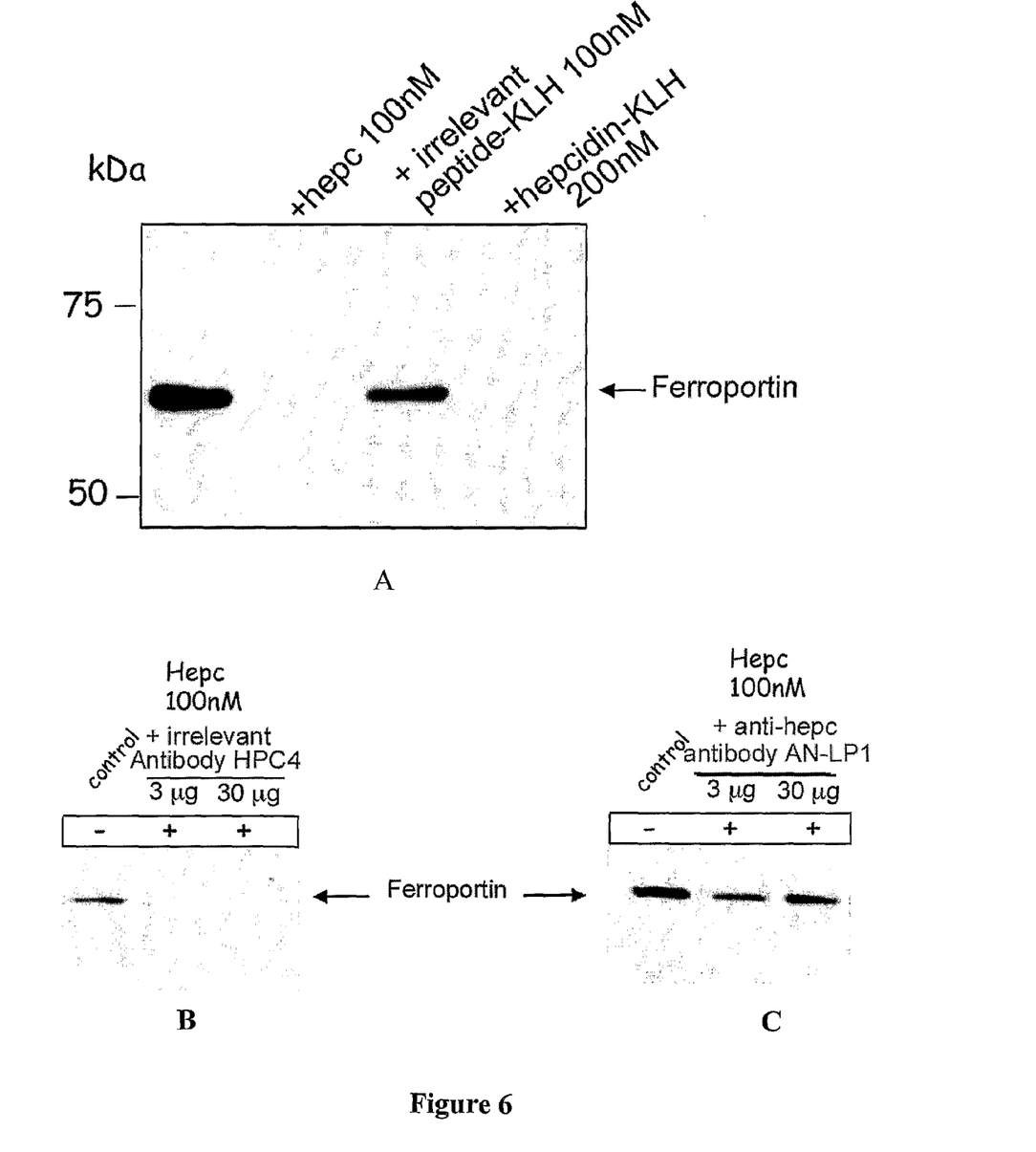
FIG. 6 (A-D) depicts functional assays for AN-LP1. (A) hepcidin alone or linked to KLH can degrade ferroportin. (B) hepcidin with antibody HPC4 degrades ferroportin. (C) hepcidin preincubated with AN-LP1 inhibits ferroportin degradation. (D) effect of increasing AN-LP1 concentration, relative to hepcidin concentration.

These results show that hepcidin alone or linked to KLH induces ferroportin degradation, while the irrelevant peptide has no effect.

The same experiment was repeated with synthetic hepcidin-25 (100 nM) preincubated for 1 hour at 37° C. with 3 or 30 μg of AN-LP1 or of the irrelevant antibody HPC4, before addition to the cell culture.

The results are illustrated by FIGS. 6B (hepcidin preincubated with the irrelevant antibody HPC4) and 6C (hepcidin preincubated with the antibody AN-LP1), and 6D (effect of increasing concentrations of AN-LP1).

These results show that while hepcidin normally induces the degradation of ferroportin in the presence of the irrelevant antibody, the binding of the AN-LP1 antibody to hepcidin neutralizes its action, thus preventing the internalisation and the degradation of ferroportin.

EXAMPLE 3

Affinity of the Hepcidin/AN-LP1 Interaction

Immobilization of the Ligands onto the Sensor Surfaces

To estimate AN-LP1 affinity constant and the antibody-antigen interactions, surface plasmon resonance (SPR) measurements were performed with a BIAcore 2000 instrument using carboxymethylated dextran CM5 chips (BIAcore, Piscataway, N.J.). AN-LP1 mAb, diluted at 2 μg/ml in 5 mM maleate buffer (pH 5.75), was immobilized on the CM5 chips by amine coupling.

Binding Assays and Data Analysis

Hepcidin was diluted in running buffer HBS-EP (0.01M HEPES pH 7.4; 0.15M NaCl, 3 mM EDTA and 0.005% polysorbate 20). Analyte was injected in 3 min, 60 μL/min injections and dissociation was monitored during 10 min. Surface Ab were generated by a 30-s to 1-min injection of glycine-HCL 10 mM pH 2. Kinetic rate constants were determined with purified antibodies. Concentrated hepcidin (0.39 nM to 12.5 nM) were injected over the chip surface at a rate of 60 μL/min to collect binding data. Data analyses were carried out with the BIAevaluation 3.0 software.

Figure 7:
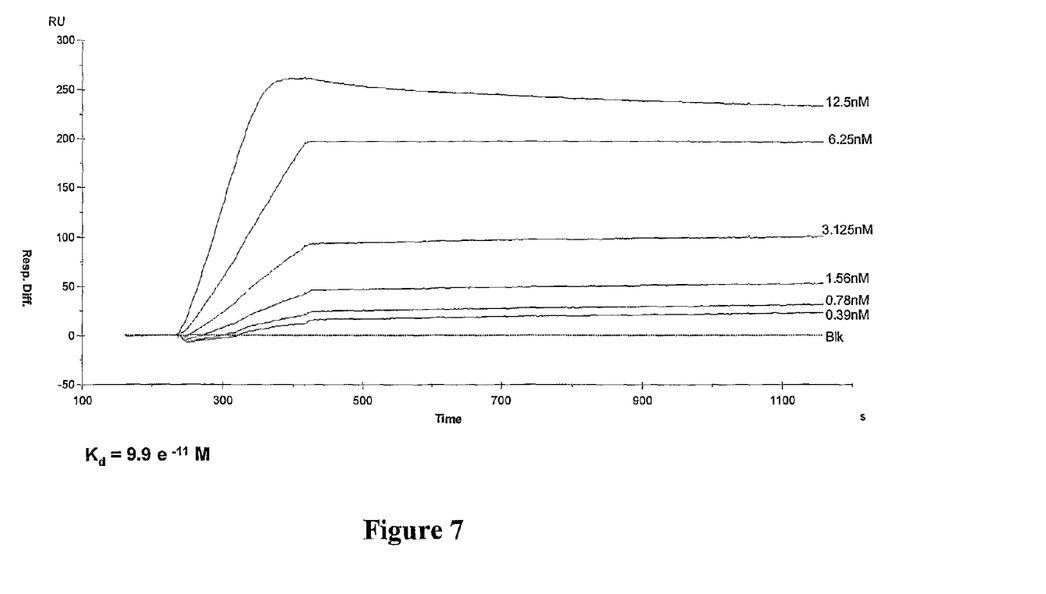
FIG. 7 depicts binding assay results of AN-LP1 to different concentrations of hepcidin.

The results are shown on FIG. 7. The concentration of hepcidin is indicated for each curve (Blk=blank).

The affinity constant (Kd) of AN-LP1 is of $9.9 \times E^{-11}$ M.

The invention claimed is:

1. An isolated antigen-binding protein that binds human hepcidin-25, comprising at least the complementarity determining region (CDR) regions 1, 2, and 3 of the variable domain of the heavy chain and the CDR regions, 1, 2 and 3 of the variable domain of the light chain of the antibody designated as AN-LP1 produced by the hybridoma deposited at Collection Nationale De Cultures De Microorganismes under the Budapest Treaty on Aug. 14, 2007 at deposit No. CNCM I-3794.

2. An isolated antigen-binding protein according to claim 1, wherein said antigen-binding protein is selected from the group consisting of:
   a) the monoclonal antibody AN-LP1 produced by the hybridoma CNCM I-3794;
   b) the antigen binding fragments of the antibody AN-LP1;
   c) the chimeric or humanized antibodies obtained from AN-LP1; and
   d) the antigen-binding fragments of the antibodies c) above.

3. An isolated antigen-binding protein according to claim 1, wherein said antigen-binding protein is able to inhibit the binding of hepcidin to ferroportin.

4. An isolated polynucleotide encoding an antigen-binding protein according to claim 1.

5. An expression vector comprising a polynucleotide of claim 4.

6. An isolated host cell expressing an antigen-binding protein transformed by an expression vector of claim 5.

7. A recombinant cell expressing an antigen-binding protein according to claim 1.

8. An isolated antigen-binding protein, comprising a VH-CDR 1 encoded by the sequence of SEQ ID NO:2, a VH-CDR 2 encoded by the sequence of SEQ ID NO:3 and a VH-CDR 3 encoded by the sequence of SEQ ID NO:4 and a variable light chain-CDR 1 (VL-CDR1) encoded by the sequence of SEQ ID NO:6, a variable light chain CDR 2 encoded by the sequence of SEQ ID NO:7 and a variable light chain CDR 3 encoded by the sequence of SEQ ID NO:8, wherein said isolated antigen binding protein binds human hepcidin-25.

9. An isolated antigen-binding protein, comprising a heavy chain variable domain encoded by the sequence of SEQ ID NO: 1 and a light chain variable domain encoded by the sequence of SEQ ID NO:5.

10. An isolated hybridoma deposited at Collection Nationale De Cultures De Microorganismes under the Budapest Treaty on Aug. 14, 2007 at deposit No CNCM I-3794.

11. A method for preparing an antigen-binding protein, comprising the steps of culturing at least one cell of claim 7, under conditions suitable to express the protein and recovering said protein from said culture.

12. A method for detecting hepcidin, and/or evaluating its amount in a biological sample from a human subject, wherein said method comprises contacting said sample with an antigen-binding protein of claim 1, under conditions allowing the formation of an immune complex between hepcidin and said antigen-binding protein, and detecting or measuring the immune complex formed.

13. A method for diagnosing a disease associated with abnormal hepcidin levels, wherein said method comprises
   obtaining a biological sample from a human subject;
   contacting said sample with an antigen-binding protein of claim 1 under conditions allowing the formation of an immune complex between hepcidin and said antigen-binding protein;
   detecting or measuring the immune complex formed; and
   comparing the detected or measured amount of immune complex with a control value of hepcidin in a normal subject, wherein a diagnosis of the disease is made when the amount of immune complex detected or measured is different from the control value.

* * * * *